United States Patent [19]

Cancedda et al.

[11] Patent Number: 5,298,417
[45] Date of Patent: Mar. 29, 1994

[54] CRYOPRESERVED IN VITRO CULTURED EPITHELIAL TISSUE AND METHOD

[75] Inventors: Ranieri Cancedda; Michele De Luca, both of Genoa, Italy

[73] Assignee: Istituto Nazionale per la Ricerca Sul Cancro, Genoa, Italy

[21] Appl. No.: 799,752

[22] Filed: Nov. 25, 1991

Related U.S. Application Data

[63] Continuation of Ser. No. 165,478, Mar. 8, 1988, abandoned.

[30] Foreign Application Priority Data

Jun. 23, 1987 [IT] Italy .............................. 21005 A/87

[51] Int. Cl.$^5$ ...................... A01N 1/02; A01N 37/18; C12N 5/00; A61K 37/00
[52] U.S. Cl. ........................... 435/240.1; 435/240.23; 435/240.241; 435/1; 514/2; 514/21; 424/574
[58] Field of Search ......... 435/240.1, 240.23, 240.241, 435/1, 240.1; 514/12, 21; 424/574

[56] References Cited

U.S. PATENT DOCUMENTS

| | | | |
|---|---|---|---|
| 3,940,943 | 3/1976 | Sikes et al. | 62/64 |
| 3,943,993 | 3/1976 | Smith | 165/2 |
| 4,016,036 | 4/1977 | Green et al. | 195/1.8 |
| 4,304,866 | 12/1981 | Green et al. | 435/240 |
| 4,456,687 | 6/1984 | Green et al. | 435/241 |
| 4,673,649 | 6/1987 | Boyce | 435/240.25 |

FOREIGN PATENT DOCUMENTS

0364306 4/1990 European Pat. Off. .
WO8001350 7/1980 PCT Int'l Appl. ........... A01N 1/02

OTHER PUBLICATIONS

Pittelkow et al, Mayo Clinic Proceedings, V. 61, 771–777, 1986.
Rosenquist et al., Journal of Burn Care, vol. 9, (Jan.-/Feb. 1988) 52.
Heimbach et al., Annals of Surgery (Sep., 1988) 317.
Konstantinow et al., Annals of Plastic Surgery (Jan. 1991) 89–97.
Green, Cell., vol. 11 (Jun. 1977) 405–416.
Pittlekow et al., J. Invest. Dermatol. (1986) 413–14.
AATB Procedure Manual, D3.310 Skin Preparation Method #1 (Mar. 1990).
Max et al. Recent Developments in Skin --- 1984. J. of MAG 73:233–236.
May et al. Cryopreservation of Skin --- 1985. Cryobiology 22:205–214.
Baxter et al. Cryopreservation of Skin --- 1985 Transplantation proceedings XVIII No. 6 Suppl 4 pp. 112–120.
"Cultured Epithelium as a Skin Substitute", Eldad, A. et al. Burns 13(3):173–180 (1987).
"The Effects of Cryoprotective Agent on the Viability of Cryopreserved Skin", Chang, Z. H. et al., Abstr., Cryobiology 23(6):573–74 (1986).
"Toxic Epidermal Necrolysis: An Approach to Management using Cryopreserved Allograft Skin", Birchall, N. et al., *Journal of Amer. Acad. of Dermatology* 16(2):368–372 (1987).
"Histoincompatible Skin and Marrow Grafts in Rabbits on Cyclosporin A", Gratwohl, A., et al., *Transplantation* 33(4):361 ∝ 364 (1982).
"Antigenicity of Venous Allografts", Axthelm, S. C. et al., *Annals of Surg.* 189(3):290–293 (1979).
"Clinical Experience with Allograft Implantation", Mankin, H. J. et al., *Clinical Orthopaedics and Related Res.* 74:69–86 (1983).

(List continued on next page.)

*Primary Examiner*—Robert J. Hill, Jr.
*Assistant Examiner*—Gian P. Wang
*Attorney, Agent, or Firm*—Testa, Hurwitz & Thibeault

[57] ABSTRACT

A process for preserving cultured epidermal sheets by incubating the sheets at room temperature in media with a glycerol or dimethylsulfoxide cryopreservant for a predetermined period of time and then freezing the cultured sheets. The cooling gradient is characterized as having a lower initial rate of cooling followed by a higher rate of cooling.

13 Claims, 1 Drawing Sheet

OTHER PUBLICATIONS

"Cryopreservation of Skin Using An Insulated Heat Sink Box Stored at −70 C", May, S. R. et al., *Cryobiology* 22:205–214 (1985).

"Recent Developments in Skin Banking and the Clinical Uses of Cryopreserved Skin", May, R. S. et al., J. of MAG. 73(1) 233–236 (1984).

"Cyropreservation of Human Fetal Organs", Groscurth, P. et al., Anat. Embryol. 174:105–113 (1986).

"Frequency and Coordination of Ciliary Beat after Cryopreservation of Respitory Epithelium", Wulffraat, N. M. et al., *Cryiobiology* 22:105–110 (1985).

"Clinical Experience with Viable Frozen Human Skin and a Frozen Skin Bank", Bondoc C. C. et al., Annals of Surgery, 174(3):371–382 (1971).

"Optimum Warming Rates for Skin Cryopreservation", May, S. R., et al., *Cryobiology* 21 (6):714, Abstract No. 87 (1986).

"Hypothermic Preservation of Skin: A Review of Current Knowledge and Application", May, S. R., *Cryobiology* 23(6):569, Abstract No. 63 (1986).

"Comparison of Dimethyl Sulfoxide and Dimethyl Sulfone as Cryoprotective Compounds", McGann, L. E. et al., *Cryobiology* 23(6):574 Abstract No. 74 (1986).

"Emerging Technologies heavy on Biotechnology Start-ups", Biotechnology Newswatch, Monday, May 16, 1988.

"Growth of Human Mammary Epithelial Cells on Collagen Gel Surfaces", Yang, N.-S. et al., Cancer Research 41: 4093–4100 (1981).

"Serial Cultivation of Single Keratinocytes From the Outer Root Sheath of Human Scalp Hair Follicles", Limat, A. et al., *Journal of Investigative Dermatology,* 87(4):485–488 (1986).

"Simple, Economical Skin Cryopreservation", Cuono, C. B. et al., Shock Infection and Burns, pp. 114–115.

"Skin Preservation by Programmed Freezing", Blondet, R. et al., *British Journal of Plastic Surgery* 35:530–536 (1982).

"Cryopreservation of Skin: A Review", Baxter, C. et al., Transplantation Proceedings, vol. XVII(6):112–120 (1985).

"Cryopreservation of Skin: Discussion and Comments", Taylor, A. C., *Cryobiology* 3(2) 192–196 (1966).

"Skin Storage in Liquid Nitrogen", Biagini, G. et al. *Journal of Cutaneous Pathology* 6:5–17 (1979).

"A Simple Device and Procedure for Successful Freezing Cells in Liquid Nitrogen Vapor", Kasten, F. H. et al., In: *Methods in Cell Biology,* vol. 14, pp. 165–179 (1976).

"Skin Cryopreservation", Praus, R. et al., Cryobiology 17:130–134 (1980).

Biological Abstracts, vol. 80(6) #54412, Sep. 15, 1985.

Jakoby et al. *Cell Culture LVIII.* pp. 30–31, 86. 1979 Academic Press N.Y.

FIG. 1a
FIG. 1b
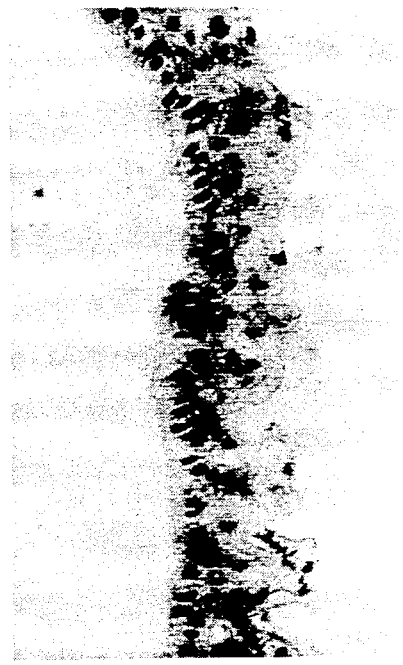
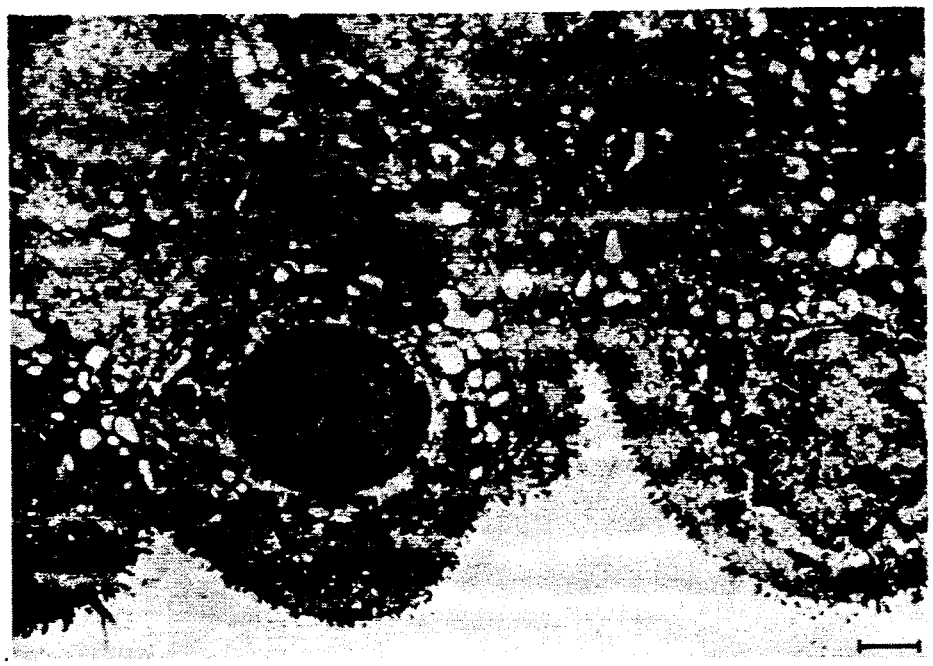
FIG. 2

CRYOPRESERVED IN VITRO CULTURED EPITHELIAL TISSUE AND METHOD

This is a continuation of copending application Ser. No. 07/165,478 filed on Mar. 8, 1988, now abandoned.

BACKGROUND OF THE INVENTION

1. Field of the Invention

The present invention generally relates to the cryologic preservation of cellular tissue. More particularly, the present invention relates to the cryologic preservation of epidermis sheets obtained by cellular culture.

2. Brief Description of the Background Art

Despite recent progress in treating burnt tissue (i.e., tissue which is characterized by sufficient amounts of denatured protein to result in cell injury or death), the death-rate of burn victims still remains unacceptably high. Such fatality levels are, of course, highly dependent on the patient's age and on the percentage of burnt body area. The death-rates are, in fact, dramatically high for third degree burns (i.e., when full-thickness dermis has been destroyed) of 50-60% or more body area. In these cases, especially, in addition to the immediate problems of advanced cardio-vascular shock and the threats of somewhat less-imminent sepsis or hydroelectrolytic impairment, yet another (slightly delayed) problem is caused by the absence of a cutaneous covering over a large body area. The difficulty with such missing coverings, or open areas, is that they tend to not spontaneously recover, since they have been completely damaged or destroyed throughout their whole thickness.

When the normally closed epithelial barrier is opened to the outside environment, a chronic pathological condition is created which, together with the above identified infective and metabolic complications, progressively worsen the patient's local and systemic conditions. The sum total of these problems often overwhelms the burn victim, who freguently dies.

It is therefore evident, once the emergency phase of treatment has been overcome, that the main medical problem is to cover the cutaneous deficit as quickly and as effectively as possible. According to conventionally accepted medical practice, wound areas are covered by transplanting split thickness tissue pieces removed from healthy unburnt regions (autografts). However, when the burnt area exceeds, for example, 60-70%, there is usually insufficient donor tissue available for grafting. Moreover, the auto graft donor site itself provides yet additional areas which lack whole cutaneous coverage. These drawbacks must be considered together with the facts that autograft donor sites also tend to recover slowly and may yield deleterious healing residues.

It is also medically acceptable to cover the cutaneous deficit by the transplantion of homologous cadaver skin, lyophilized heterologous skin (from, for example, pig), synthetic artificial cutis and the like. However, these alternate materials, being allogenic will slough spontaneously within 1-6 months, and they must eventually be replaced with autologous tissue and are thus, at best, temporary in nature.

Methods recently disclosed in U.S. Pat. Nos. 4,016,036; 4,304,866 and 4,456,657 teach methods for culturing human epithelial films obtained from cutaneous keratinocytes. These films, of course, may be autologous and therefore would allow burnt areas to be covered without being subject to later rejection or sloughing. These methods in these U.S. patents are based on the removal of a small (2-3 cm$^2$) piece from a healthy donor area. An epithelial cellular suspension obtained using the donor tissue is then cultured and expanded through subsequent inoculations of the primary culture. When the secondary and tertiary cultures become confluent, multi layered sheets of epithelium can be obtained.

Thus, several serious problems are potentially overcome, such as the poor availability of residual healthy skin in the seriously burnt patient or the need to use expensive pig, cadaver, or artificial cutis, each of which may not be readily available and whose use may be strictly regulated because of antibody reaction.

On the other hand, the keratinocytes cultures obtained according to the above methods require from 3-4 weeks until they are suitably expanded so that film sheets may be obtained. In other words, the burnt patient must remain without protection of the burnt areas for the initial 3-4 weeks. This initial period is, of course, the most critical and so, that period during which the graft of healthy cutis would be most highly beneficial. Additionally, the cultured epithelial sheets taught in these U.S. patents must be used within a few hours of harvesting since it has not been possible to develop a conservation method which can maintain expanded epidermis sufficiently to allow their travel to distant user centers.

The availability of frozen cultured epithelium is advantageous also for those patients that require several transplantations, since it facilitates a better coordination between culture and surgical schedules.

Therefore, it is now possible to realize the institution of "tissue banks" or other depositories of allogeneic expanded epidermis which could be relied upon in the event of emergency.

Readily available cultured allografts in a frozen state can have several clinical applications. For example the present inventors have evidence that deep second degree burns heal much faster when grafted into cultured allografts. Limited full thickness lesions clinically appearing as third-degree burns were reepithelialized by the recipient keratinocytes, whose growth and probably migration were strongly stimulated by cultured allografts.

Cultured allografts could also be applied in most of donor sites utilized for split thickness mesh grafts. This results in a nice healing of those areas even after 4 days.

The method described herein can be successfully utilized also for cryologic preservations of mucosa expanded in vitro. In this regard, the present inventors have determined that expanded mucosa can be obtained in vitro starting from a punch biopsy following the methodology described for production of epithelial films from cutaneous keratinocytes. The present inventors have also determined that the in vitro expanded mucosa can be successfully transplanted in patients that require oral mucosa transplant.

SUMMARY OF THE INVENTION

The present invention provides a process for preserving transplantable sheets of epithelium which has been cultured in vitro.

The present invention also enables the transport of preserved cultivated epidermis and therefore, the institution of a bank of cryopreserved expanded allogenic epidermis.

According to the present invention, cultivated epidermal sheets which are otherwise ready to be grafted are incubated in media containing conventional nutritive agents and a cryopreservative agent. The sheets are incubated for a predetermined period of time and thereafter frozen to a final temperature of about −100° C. The cooling gradient utilized is characterized by a slower initial phase and a faster final phase.

BRIEF DESCRIPTION OF THE DRAWINGS

FIGS. 1a is an optical micrograph of a cultured human epithelial sheet before being treated in accordance with the present invention;

FIG. 1b is an optical micro graph of the cultured epithelial sheet of FIG. 12, which has been treated in accordance with the present invention and then thawed; and FIG. 2 is an electron micrograph of the cultured epithelial sheet of FIG. 1b.

DETAILED DESCRIPTION OF THE INVENTION

The present invention utilizes sheets of epithelial films, and the like, such as those which are produced in accordance with U.S. Pat. Nos. 4,016,036, 4,304,866 and 4,456,657, discussed above, which patents are hereby expressly incorporated herein. The sheets are first stabilized by being incubated in media, preferably nutrient media, containing a cryopreservative agent. The cyopreservative agent is preferably contained at from about 8-15 wt. %, and is prefereably glycerol or dimethylsulfoxide. Most preferably, the cryopreservative is glycerol which is used at about 10 wt. %. The sheets are incubated at about room temperature, preferably for not more than 15 minutes.

In this regard, the incubation time has been found to be somewhat critical since the present inventors have determined that the length of such periods dramatically affects cell viability and the ability of transplanted keratinocytes to form colonies. In particular, tests carried out which vary the period of incubation reveal a rather remarkable decrease in the ability of the keratinocytes to form colonies after both very short incubation times (of less than about 2 minutes) and fairly long times (of more than about 15 minutes), whereas the ability to form colonies greatly increases at times of about 4-7 minutes and is maximized at periods of about 5-7 minutes.

After incubation, the epithelial sheets are subjected to a freezing procedure wherein temperature is strictly controlled, such that the rate of the temperature dr op is slower at the start of the procedure than at the end of procedure. At the culmination of freezing, the now-frozen sheets have preferably reached at most −80° C., and most preferably at most −100° C. In this state, the treated epithelial sheets may be maintained for at least about 3 months without substantially changing their morphological and functional characteristics. In fact, pieces of epithelial sheets obtained by treatment in accordance with the present invention are completely equivalent in terms of both morphology and graftability to those which are otherwise obtainable from fresh cultures which have not been subjected to cryopreservation.

In this regard, FIG. 1a illustrates a sheet before being subjected to the process of the present invention, whereas the FIG. 1b refers to a sheet which has been subjected to the freezing process of the present invention and has also been defrosted. The sheet of FIG. 1b is, therefore, ready for use as a transplant. Both sheets of FIGS. 1a and 1b have been fixed, incorporated, cut and dyed with hematoxylin eosine. FIG. 2 is an electron micrograph of the in vitro cultivated epidermal sheet of FIG. 1b. From these micrographs, it is evident that the present invention results in good cell conservation of the basal layer as well as the good conservation of intercellular structure.

When the treated sheets are to be used, it is sufficient to incubate them about at 37° C. for a few minutes, followed by washing in physiological saline or in suitable culture media.

In addition to the coverage of burnt areas, the preserved epidermis sheets should find useful applications in other fields such as, for instance, in oncologic plastic or reconstructive surgery. The preserved in vitro expanded mucosa can also be utilized in oral surgery.

The following example further illustrates one preferred embodiment of the method of the present invention, but is neither intended nor to be considered as limitative in scope.

EXAMPLE

The keratinocytes cultures were obtained utilizing the procedures of the U.S. patents identified above which were incorporated herein. In particular, the confluent secondary keratinocyte cultures obtained according to U.S. Pat. No. 4,016,036 were detached from their culture bottles, transferred on vaseline coated gauze and anchored by means of metallic vascular surgery clips according to the method disclosed in U.S. Pat. No. 4,304,866. These cultivated tissue pieces were then transferred under sterile conditions in 12×20 cm sterile polyester/ polyethylene/aluminum bags (Gambro S.A.—18, rue de Calais —75009 Paris) (3 grafts in each ba g). 100 ml of media was then added to the bags, wherein the media comprised:

| Dulbecco modification of Eagle's medium | 54 wt. % |
|---|---|
| Ham's F12 | 27 wt. % |
| fetal calf serum (FCS) | 9 wt. % |
| glycerol | 10 wt. % |
| glutamine | 4 mM |
| adenine | $1.8 \times 10^{-4}$M |
| insulin | 5 mcg/ml |
| transferrine | 5 mcg/ml |
| triiodothyronine | $2 \times 10^{-9}$M |
| hydrocortisone | 0.4 mcg/ml |
| epidermal growth factor | 10 ng/ml |
| penicillin streptomycine | 50 U/ml |

The bags were thermally sealed and incubated at room temperature for between 5-7 minutes. The bags were placed in a suitable container and transferred into a suitable programmable freezer (one such freezer is known as the Programmable Temperature Controller PTC-300 and is commercially available from Planer Products, Ltd.). The tissue pieces were then frozen using following freezing program.

| Starting temperature: | +25° C.; |
|---|---|
| −5° C./min. to | +3° C.; |
| pause for 4 min.; | |
| −1° C./min. to | −7° C.; |
| −25° C./min. to | −40° C.; |
| +15° C./min. to | −25° C.; |
| −2° C./min. to | −40° C.; |
| and | |

-continued

| | |
|---|---|
| −3° C./min. to | −100° C. |

When the final temperature of −100° C. was attained, the plastic bags were transferred in a suitable metal container which was previously cooled to −80° C. at least 2 hours earlier. The metal container was then rapidly transferred to a −80° C. freezer.

The bags containing the frozen epithelial sheets may be sent to long distances provided only that temperature increases are avoided. The frozen sheets may be preserved to −80° C. for at least 3 months, while maintaining their morphological and functional characteristics.

When it is necessary to use the frozen films, the bags are removed from the freezer, immediately immersed in a water bath at +37° C. and incubated for about 10 minutes. The bags are then immersed for a few seconds in 70% ethanol. The bags are then opened in sterile conditions, the epithelial sheets are removed, transferred in sterile containers, throughly washed with culture medium or physiological saline and used.

It will be appreciated, of course, that various modifications of the foregoing procedures are within the purview of those skilled in the art and that such modifications and the like are intended to be covered by the claims which follow.

We claim:

1. A cryopreserved epithelial wound repair tissue comprising a frozen, confluent sheet of allogenic in vitro cultured epithelial tissue which, after being stored at a temperature of about −80° C., thawed and applied to the surface of a wound in a patient, maintains morphological and functional characteristics sufficient to induce wound healing in said patient.

2. The tissue of claim 1 wherein the epithelial tissue are keratinocytes.

3. The tissue of claim 1 further comprising a backing disposed in contact with a surface of the sheet.

4. The tissue of claim 3 wherein the backing comprises a material adapted for removal from the surface of said sheet.

5. A method for cryopreserving sheets of in vitro cultured epithelial tissue, comprising the steps of:
 a) incubating the epithelial sheets detached from culture vessels for from about 2 minutes to about 15 minutes at room temperature in media containing a cryopreservant; and
 b) freezing said epithelial sheets utilizing a gradient of cooling comprising:

| | |
|---|---|
| Starting temperature: | +25° C.; |
| −5° C./min. to | +3° C.; |
| pause for 4 min.; | |
| −1° C./min. to | −7° C.; |
| −25° C./min. to | −40° C.; |
| +15° C./min. to | −25° C.; |
| −2° C./min. to | −40° C.; |
| and | |
| −3° C./min. to | −100° C. |

6. The method of claim 5 further comprising storing the epithelial sheets at about −80° C.

7. The method of claim 5 wherein the cryopreservant is present at a concentration of about 8 to 15 percent by weight of the media.

8. The method of claim 7, wherein said cryopreservant is glycerol or DMSO.

9. The method of claim 5, wherein the period of room temperature incubation is from about 4 minutes to about 7 minutes.

10. The method of claim 5 further comprising thawing the frozen tissue.

11. The method of claim 7 wherein the thawing step comprises incubating the tissue at about 37° C.

12. The method of claim 10 wherein the epithelial sheets are stored for at least three months.

13. The method of claim 12 wherein the thawed sheets upon application to a wound, are capable of mitosis and stratified differentiation.

* * * * *

UNITED STATES PATENT AND TRADEMARK OFFICE
CERTIFICATE OF CORRECTION

PATENT NO. : 5,298,417
DATED : March 29, 1994
INVENTOR(S) : Ranieri Cancedda, et al.

It is certified that error appears in the above-indentified patent and that said Letters Patent is hereby corrected as shown below:

Column 5,
Claim 1 should be corrected to read:

A cryopreserved epithelial wound repair tissue comprising a frozen, confluent sheet of in vitro cultured epithelial tissue characterized in that, after being stored at a temperature of at most -80°C, thawed and applied to the surface of a wound in a patient, maintains morphological and functional characteristics sufficient to induce wound healing in said patient.

Signed and Sealed this

Eleventh Day of October, 1994

Attest:

BRUCE LEHMAN

*Attesting Officer*  *Commissioner of Patents and Trademarks*